(12) United States Patent
Gebrayel

(10) Patent No.: US 6,814,261 B1
(45) Date of Patent: Nov. 9, 2004

(54) MOUTHWASH DISPENSER

(76) Inventor: Nehme Gebrayel, 34016 Valencia Dr., Leesburg, FL (US) 34788

( * ) Notice: Subject to any disclaimer, the term of this patent is extended or adjusted under 35 U.S.C. 154(b) by 0 days.

(21) Appl. No.: 10/321,740

(22) Filed: Dec. 17, 2002

(51) Int. Cl.⁷ ................................................. B67D 5/58
(52) U.S. Cl. .................... 222/181.3; 222/192; 222/156; 222/504
(58) Field of Search ............ 222/52, 63, 181.1–181.3, 222/182, 504, 185.1, 192

(56) References Cited

U.S. PATENT DOCUMENTS

| | | |
|---|---|---|
| 1,384,687 A | 7/1921 | Conkling |
| 2,609,122 A | 9/1952 | Stenerson |
| 3,434,629 A | 3/1969 | Hooge et al. |
| 3,604,592 A | 9/1971 | Bacon |
| 3,896,977 A * | 7/1975 | Bergstrom .................. 222/353 |
| 3,987,932 A | 10/1976 | Maldon |
| 4,257,538 A | 3/1981 | Fowler |
| 4,946,070 A * | 8/1990 | Albert et al. .................. 222/52 |
| 5,215,193 A | 6/1993 | Dennis |
| 5,255,822 A * | 10/1993 | Mease et al. .................. 222/63 |
| 5,275,305 A | 1/1994 | Gross |
| 5,713,492 A | 2/1998 | DeGennaro |
| 6,036,056 A * | 3/2000 | Lee et al. ..................... 222/63 |
| 6,244,470 B1 | 6/2001 | Harley-Wilmot |

* cited by examiner

*Primary Examiner*—Kenneth Bomberg
*Assistant Examiner*—M A Cartagena
(74) *Attorney, Agent, or Firm*—Michael I. Kroll

(57) ABSTRACT

A mouthwash dispenser comprising a housing having an inner cavity able to retain a liquid therein and an opening providing access to said inner cavity, a lid for selectively sealing said opening and thereby enclosing the liquid in said inner cavity of said housing, control means extending from said housing for selectively dispensing said liquid from said inner cavity, and a spout connected to said inner cavity for dispensing liquid from said inner cavity, wherein said control means is moveable between a first position preventing a flow of liquid from said inner cavity to said spout and a second position for allowing a flow of liquid from said inner cavity to said spout.

12 Claims, 14 Drawing Sheets

MOUTHWASH DISPENSER

BACKGROUND OF THE INVENTION

1. Field of the Invention

The present invention relates generally to oral hygiene and, more specifically, to a device for the controlled dispensing of an oral antiseptic or mouthwash that is easily refillable. This device eliminates the multiple steps needed or required to obtain mouthwash directly from a commercial mouthwash bottle.

The device includes a housing and lid having an inner cavity for the controlled containment and dispensing of an oral antiseptic or mouthwash that can be poured into the cavity, with said housing having a transparent longitudinally extending strip of transparent material that is integral of the housing to serve as a display for the user to determine the remaining amount of the contained liquid or amount of liquid dispensed into a receptacle. Additionally the user may control the retention or release of the contained liquid by a plurality of possible methods being of but not limited to a mechanical or electrical nature that may or may not be recessed or presented with a base/platform used for the placement or guidance of a mouthwash receptacle to the dispensing position.

The housing of the present invention may be typically a cubic, cylindrical or rectangular form made of material capable of efficient containment of a liquid mouthwash or oral antiseptic. Embodiments including an electrical based valve or gate activation means may include an additional integral or separately constructed control housing to contain the necessary components required to operate the dispensing components. Dispensing of the contained mouthwash may be achieved by a plurality of methods including a valve assembly having a control handle or button to manipulate a sealing element that functions to selectively close or release the contained substance, or a spout and retention gate that may be disposed into an open or closed position by the pushing or angularly displacing a control lever, or activating a motion detecting means such an electric eye that activates a switch that supplies power to an actuator or an unpowered series of mechanical linkages that can be set in motion by application of an applied force upon the control lever.

Additional elements of the present invention include modifications upon the form and structure of the housing or housings, these modifications being areas whereby the said housing may be attached to a wall by a fastening means and/or the housing can be additionally modified to present a platform for the guidance or placement of a receptacle into position during dispensing while the present invention is attached to a wall, and a dispenser for the storage and release of receptacles to allow the user to selectively dispense the receptacles for use with the present invention when desired.

The housing may be transparent or translucent to provide a visual indicator referencing the quantity of fluid in the reservoir or a vertical indicator window may be provided. Furthermore, the housing member is decorative and may have any number of available colors or patterns and may be shaped to resemble objects of interest such as a house or a space shuttle to further enhance the aesthetic qualities thereof.

2. Description of the Prior Art

There are other oral hygiene devices designed for mouthwash or oral antiseptic. Typical of these is U.S. Pat. Nos. 1,384,687; 2,609,122; 3,434,629; 3,604,592; 15,193; 5,275, 305; 5,713,492; and 6,244,470.

In a product dispensing apparatus, a bin having a slidable valve controlling the outlet thereof, a hopper below and removably associated with the bin and having a valve controlled inlet, a slidable product receiving member in the hopper, means for retaining the member at varying determined positions relative to the valve in the hopper means for releasing said retaining means to permit the gravitating of the member through the hopper, means for limiting the movement of the member in such direction, and means for discharging the products from the member when the latter is in the lowered position.

Dentifrice cabinet comprising a base constituting a shelf and formed with a downwardly extending boss having a threaded bore open at upper and lower ends, a depending flange along a front edge of the shelf formed with an opening opposite the front portion of said boss, the boss being formed with transversely positioned opposed front and rear openings aligned with the opening in said flange, a hollow adapter screwed into the bore of said boss and open at upper and lower ends and formed in front and rear portions with openings with the openings of the boss, said adapter adapted to support a container in an inverted vertical position, and a flat strip transversely slidable through the aligned openings of the flange and the boss and the adapter and formed with an opening, the outer end of said strip being bent downwardly and forming a handle for sliding the strip transversely from a closed position in blocking relation to the hollow adaptor to an opened position in which its opening registers with the adaptor for allowing flow of material downwardly through and out of the adaptor.

A liquid dispenser comprising a housing with a vertical compartment open at both top and bottom, a removable dispensing unit in the bottom of the compartment as a closure therefore, and with a receptacle for seating the neck of an inverted bottle containing the liquid, removeable supporting means for said unit, the mouth of the bottle covered by a fragile seal, means in the receptacle bottom puncturing the seal on said seating, a liquid-dispensing conduit extending in a lateral direction from said seal-puncturing means being a flat screw head with an upward cluster of barbs, and the screw bored to communicate with said conduit.

A combination cup and liquid dispenser with a tank body made of translucent preferably plastic material for dispensing a variety of liquids. The tank body has a service cap closing an access opening permitting easy cleaning and maintenance. A metal clip is removably mounted on the tank body forming a cup holder and dispenser in cooperation with the tank body. The tank body and clip may be mounted inside a cabinet for normal use by a metal-retaining clip and may be removed easily for refilling and cleaning.

A housing is attached to a restroom wall. Inside the housing is a first means that can release the bottom cup from a stack of disposable cups stored in the housing. A second means can introduce mouthwash inside the released cup when operated. A conventional tube of toothpaste is supported in a frame inside the housing, in a vertical, downwardly pointed position. Both the first and second means are controlled by push buttons that are located on the front of the housing. Another push button located on the front of the housing can cause the toothpaste tube to be squeezed when pressed, causing toothpaste to be squeezed downwardly out of the tube.

A liquid dispenser, for dispensing discreet amounts of a liquid, such as a mouthwash, comprised of a container for a supply of a liquid and a base member which may be attached to the container in a horizontal position to provide for a free standing condition of the assembly, or, in a vertical position for suspension from a pair of screws preset in a wall. A double acting valve, provided with a laterally extending release bar, is disposed at the bottom of the container, said valve being normally spring urged into a closing relation with a discharge port in the bottom of a dose cup, fixed relative to the bottom end of the container. When the top edge of a receptacle such as a drinking glass or paper cup is pressed upwardly against the release bar, the valve is moved from the discharge port of the dose cup permitting the liquid therein to flow into the drinking glass or other receptacle, and the valve is moved into a closing relation with a discharge port opening from the container into the dose cup. When the glass or other receptacle is removed from the release bar, the dose cup port is again closed and the container port is reopened to replenish the dose cup with a discreet amount of liquid from the container.

A device arranged to include a plurality of containers mounted within a unitary housing, with a first and second container including storage for toothpaste container structure, as well as drinking cups respectively. The housing includes a third container slidably mounting a slide wall therewithin mounting toothbrushes and the like thereon, with the slide wall operative by a dental floss container slidably mounted to a front wall of the housing. A mouthwash dispenser is mounted at an intersection of the first side wall and fluid container utilizing a valve member to effect dispensing of predetermined quantities of mouthwash fluid therefrom.

A refillable or disposable mouthwash and cup dispensing system incorporating a handle effect from the dispenser and cooperating with a wall mounted bracket to simplify removal and refilling. A mechanism for conserving the taps from dispensable units is disclosed.

The mouthwash dispensing device includes a frame having first and second reservoirs secured thereto, the first reservoir having a first port and the second reservoir having a second port, the first and second reservoirs adapted to contain mouthwash therein. A valve assembly is associated with the first and second reservoirs for selectively gating the first and second ports. An actuating assembly is associated with the valve for opening and closing the ports to release mouthwash from the reservoirs in response to user manipulation. The frame is adapted to store both drinking cups and a bottle of mouthwash therein. A locking cover is provided to restrict access to the stored cups and mouthwash.

A measured quantity liquid dispenser including a liquid supply container and an attached liquid dispensing chamber. The dispensing chamber has a hinged lid with a locking ledge. A slide plate is moveable between a first position where flow of liquid between the supply container and the dispensing chamber is prevented and the lid of the dispensing chamber is unlocked, and a second position where flow is permitted between the supply container and the dispensing chamber and the lid of the dispensing chamber is locked. The liquid dispenser is inverted with the slide plate moved to the second position to refill the dispensing chamber. The dispenser is especially useful to limit a child's use of a liquid composition such as mouthwash or shampoo.

While these oral hygiene devices may be suitable for the purposes for which they were designed, they would not be as suitable for the purposes of the present invention, as hereinafter described.

SUMMARY OF THE PRESENT INVENTION

A primary object of the present invention is to provide a refillable mouthwash dispenser having a housing with a removable lid and spout for the selective containment and dispensing of mouthwash.

Another object of the present invention is to provide a mouthwash dispenser having a transparent display for monitoring the amount of mouthwash contained and dispensed from the housing.

Yet another object of the present invention is to provide a mouthwash dispenser that may be mounted to a wall for home or commercial use.

Still yet another object of the present invention is to provide a mouthwash dispenser having a plurality of possible dispensing means including a valve assembly with a control handle, control lever or electric eye.

Another object of the present invention is to provide a mouthwash dispenser having either a mechanical or electrical means for selectively positioning a retention gate into an open or closed position, thereby allowing or preventing the flow of mouthwash.

Yet another object of the present invention is to provide a mouthwash dispenser having a receptacle dispenser integral with the outer surface of the housing providing easy access by the user to a plurality of disposable or reusable mouthwash receptacles.

Still yet another object of the present invention is to provide a mouthwash dispenser having a base/platform to provide an area where the user may rest their mouthwash receptacle and to serve as a guide for proper placement of the receptacle during dispensing operations.

Still another objective of the present invention is to provide a mouthwash dispenser having a fill spout to accommodate a disposable mouthwash bottle equipped with a seal on it's neck wherein said seal is punctured by a piercing element during insertion into the fill spout.

Additional objects of the present invention will appear as the description proceeds.

The present invention overcomes the shortcomings of the prior art by providing a mouthwash dispenser having a housing with a removable lid and compartment whereby mouthwash may be placed therein and contained until selectively dispensed by the user by means of either a mechanical or electrically operated retention gate or valve assembly that may be operated or activated by means of a control handle, control lever or electrical presence sensing means such as an electric eye. Additionally the present invention provides a housing having a transparent display that allows the user to observe the amount of contained and or dispensed mouthwash remaining in the housing, also the housing may include a receptacle dispenser for the easy accessibility, for the user to gain access to a plurality of disposable or reusable mouthwash receptacles, and structural features that allow for the present invention to be mounted to a wall for home or commercial use.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
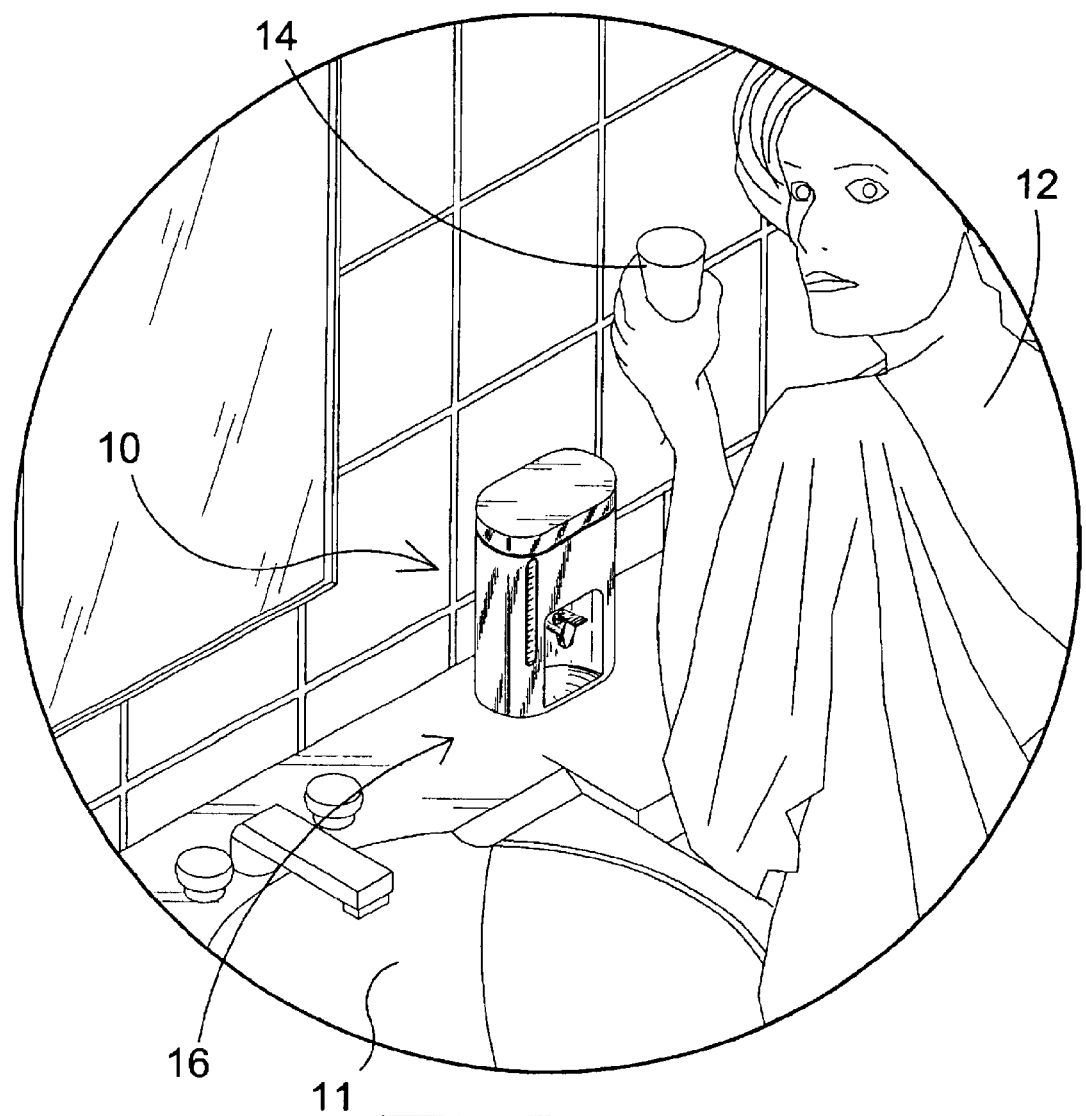
FIG. 1 is a perspective view of the mouthwash dispenser of the present invention positioned adjacent a sink for use by a user.

Turning now descriptively to the drawings, in which similar reference characters denote similar elements throughout the several views, the Figures illustrate mouthwash dispenser. With regard to the reference numerals used, the following numbering is used throughout the various drawing Figures.

10 mouthwash dispenser of the present invention
11 sink
12 user
14 receptacle
16 counter top
18 housing
recessed area
22 control mechanism
24 spout
26 display
27 hinge
28 lid
29 base of inner cavity
sealing element
31 opening of inner cavity
32 mouthwash
34 inner cavity
36 receptacle dispenser
38 receptacle compartment
39 receiving area
receptacle compartment door
41 connecting device
42 receptacle refill slot
44 compartment housing
arm
46 control housing
48 base
50 power source
52 actuator
54 switch
56 retention gate
58 fastener
60 wall
62 electric eye
64 external receptacle dispenser
66 lid
68 shelf
70 door
72 hinge
74 storage compartment
76 refill spout
78 puncture element
80 seal
81 mouthwash bottle spout
82 mouthwash bottle

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Turning now to the drawings, in which similar reference characters denote similar elements throughout the several views and embodiments, FIGS. 1–14 illustrate the mouthwash dispenser of the present invention indicated generally by the numeral 10.

FIG. 1 is a perspective view of the mouthwash dispenser 10 of the present invention positioned adjacent a sink for use by a user. The mouthwash dispenser 10 as shown herein is a freestanding, self-contained apparatus. The mouthwash dispenser 10 is preferably positioned atop a counter 16 in the bathroom of a user 12. When the user 12 desires to use mouthwash, the user takes a receptacle 14, such as a cup, and fills the receptacle 14 with mouthwash contained within the mouthwash dispenser 10. The mouthwash dispenser 10 allows for easy and clean dispensing of mouthwash for a user 12. The mouthwash dispenser 10 is also compact and fits easily atop the counter 16. Alternatively, the mouthwash dispenser 10 may be fastened to a wall, thereby allowing the user 12 to utilize the dispenser 10 without taking up valuable counter space.

Figure 2:
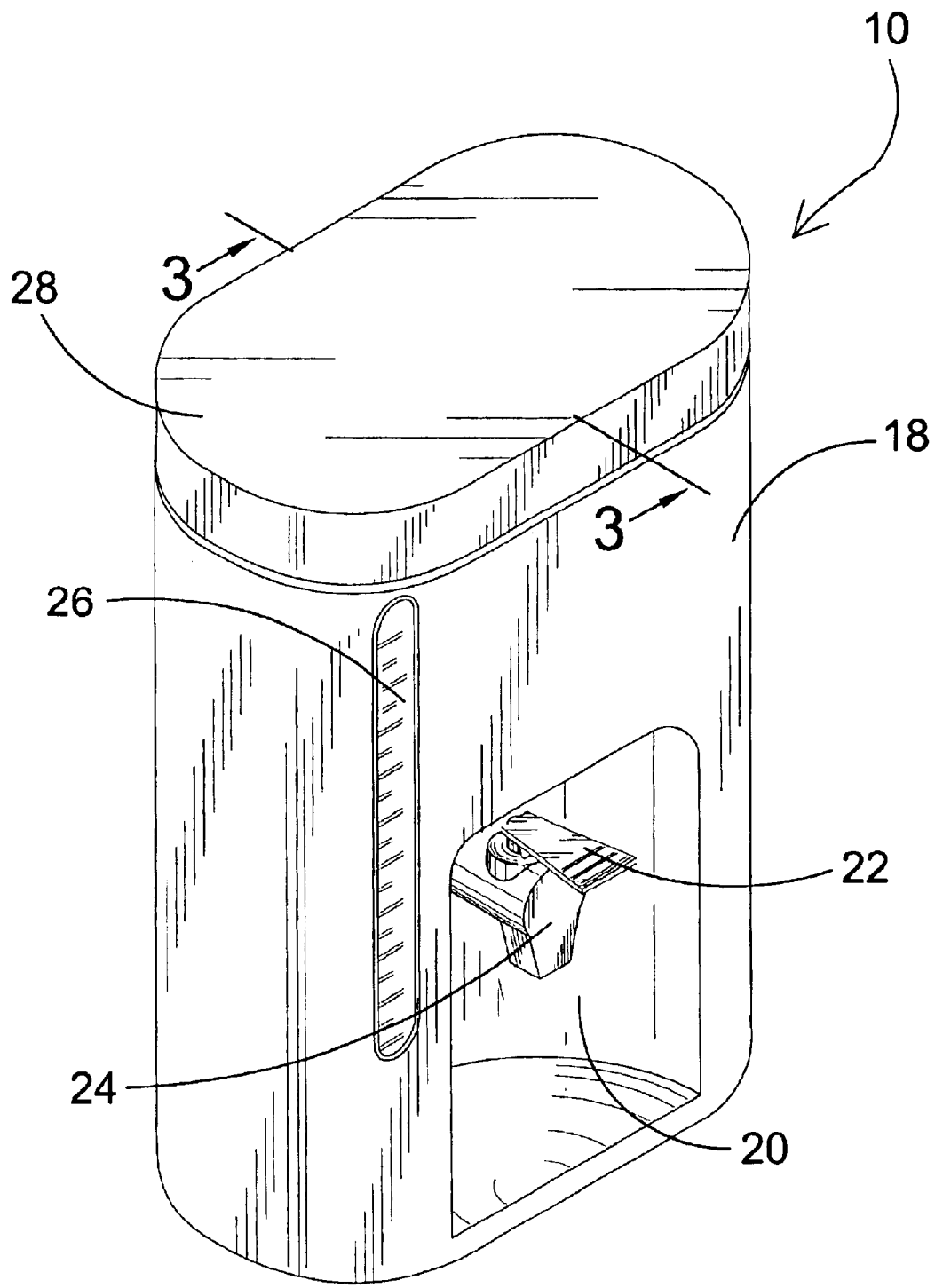
FIG. 2 is a perspective view of the mouthwash dispenser of the present invention.

FIG. 2 is a perspective view of the mouthwash dispenser of the present invention. The mouthwash dispenser 10 of the present invention includes a housing 18. The housing 18 has a recessed area 20. Within the recessed area 20 is a control mechanism 22 for controlling the disbursement of mouthwash 32 and a spout 24 for dispensing mouthwash therethrough. The dispensing of the mouthwash through the spout is controlled by the control mechanism 22. The recessed area 20 is of a size able to receive a receptacle 14 into which the mouthwash 32 is to be dispensed. The housing 18 may be transparent, translucent or opaque. The opaque housing 18 has a vertical indicator 26 providing a visual indicator for viewing the quantity of fluid remaining in the reservoir. The display 26 is preferably formed from a transparent material and provides a view into the housing. However, any display device able to allow a user 12 to determine the level of the contents remaining within the housing 18 may be used. A lid 28 is positioned on a side of the housing covering an opening therein for the insertion of mouthwash. In this figure, the lid 28 is shown positioned on a side of the housing 18 opposite the side of the recessed area 20. The lid 28 seals the opening in the housing 18 thereby enclosing the mouthwash 32 therein and preventing the mouthwash from spilling. The lid 28 is easily removable so that the user 12 can refill the mouthwash dispenser 10 when required.

Figure 3:
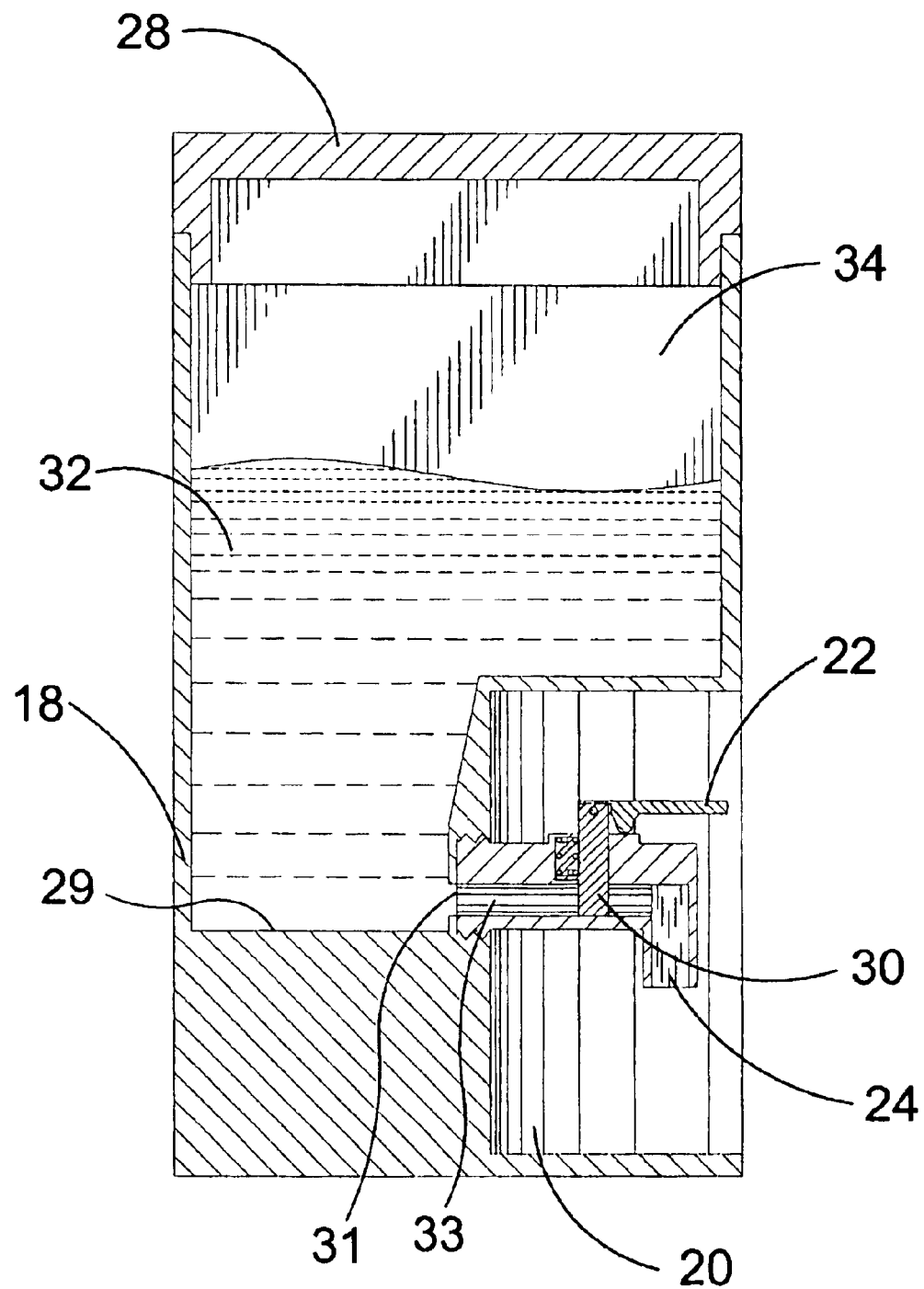
FIG. 3 is a cross-sectional view of the mouthwash dispenser of the present invention, taken along the line 3—3 of FIG. 2.

FIG. 3 is a cross-sectional view of the mouthwash dispenser of the present invention taken along the line 3—3 in FIG. 2. FIG. 3 shows the mouthwash dispenser 10 of the present invention having a housing 18. The housing 18 is hollow and contains an inner cavity 34. The inner cavity 34 contains mouthwash 32 poured therein by a user 12. A lid 28 is provided to cover the inner cavity 34 of the housing 18 and selectively seal the cavity 34. At the base 29 of the inner cavity 34 is an opening 31. A tube 33 is positioned to extend from the opening 31. At an end of the tube 33 is the spout 24. The tube 33 connects the inner cavity 34 with the spout 24. The tube 33 has a sealing element 30 that blocks the path through the tube 33 between the inner cavity 34 and the spout 24. The sealing element is moveable between a first closed position blocking the flow of mouthwash 32 through the tube 33 and a second open position allowing mouthwash to flow through the tube 33. The sealing element 30 is normally in the closed position. The sealing element 30 is controlled to move between the first closed position and the second open position by the control mechanism 22. The control mechanism 22, when activated, moves the sealing element 30 from the first closed position to the second open position allowing the mouthwash 32 contained in the inner cavity 34 to flow freely through tube 33 and spout 24 and into a receptacle 14. When the user 12 deactivates the control mechanism 22, the sealing element 30 is returned to its original first closed position within tube 33 thereby preventing the flow of mouthwash 32 through tube 33 to spout 24.

Figure 4:
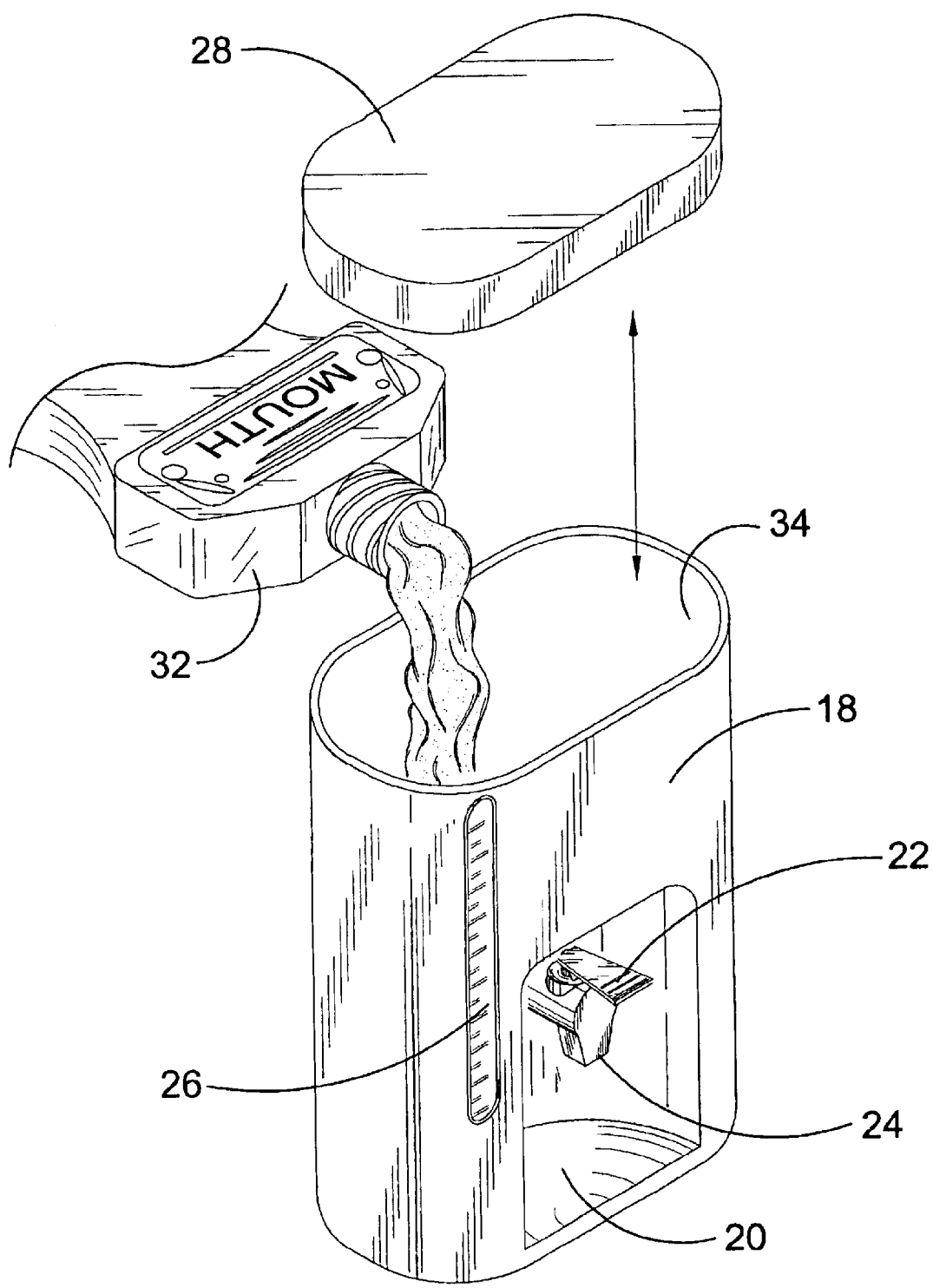
FIG. 4 is a perspective view of the mouthwash dispenser of the present invention having a top thereof removed being refilled with mouthwash.

FIG. 4 is a perspective view of the mouthwash dispenser of the present invention being refilled with mouthwash. The mouthwash dispenser 10 of the present invention includes a housing 18. The housing 18 has a recessed area 20. Within the recessed area 20 is a control mechanism 22 for controlling the disbursement of mouthwash 32 and a spout 24 for dispensing mouthwash therethrough. The dispensing of the mouthwash through the spout is controlled by the control mechanism 22. The recessed area 20 is of a size able to receive a receptacle 14 into which the mouthwash 32 is to be dispensed. The housing 18 may be transparent, translucent or opaque. The opaque housing 18 has a vertical indicator 26 providing a visual indicator for viewing the quantity of fluid remaining in the reservoir. The display 26 is preferably formed from a transparent material and provides a view into the housing. However, any display device able to allow a user 12 to determine the level of the contents remaining within the housing 18 may be used. A lid 28 is positioned on a side of the housing covering an opening therein for the insertion of mouthwash. In this figure, the lid 28 is shown positioned on a side of the housing 18 opposite the side of the recessed area 20. The lid 28 seals the opening in the housing 18 thereby enclosing the mouthwash 32 therein and preventing the mouthwash from spilling. The lid 28 is easily removable so that the user 12 can refill the mouthwash dispenser 10 when required. The lid 28 is provided for selectively sealing the inner cavity 34. The lid 28 is shown detached from the housing 18 to enable a user 12 to refill the inner cavity 34 with mouthwash 32. The user 12 is able look at the display means 26 when refilling the dispenser 10 with mouthwash 32 to determine the amount of mouthwash within the inner cavity 34 and thereby prevent overfilling the dispenser 10. When the inner cavity 34 has been refilled, the lid 28 is replaced back on top of the housing 18 thereby re-forming a seal between the lid 28 and the housing 18.

Figure 5:
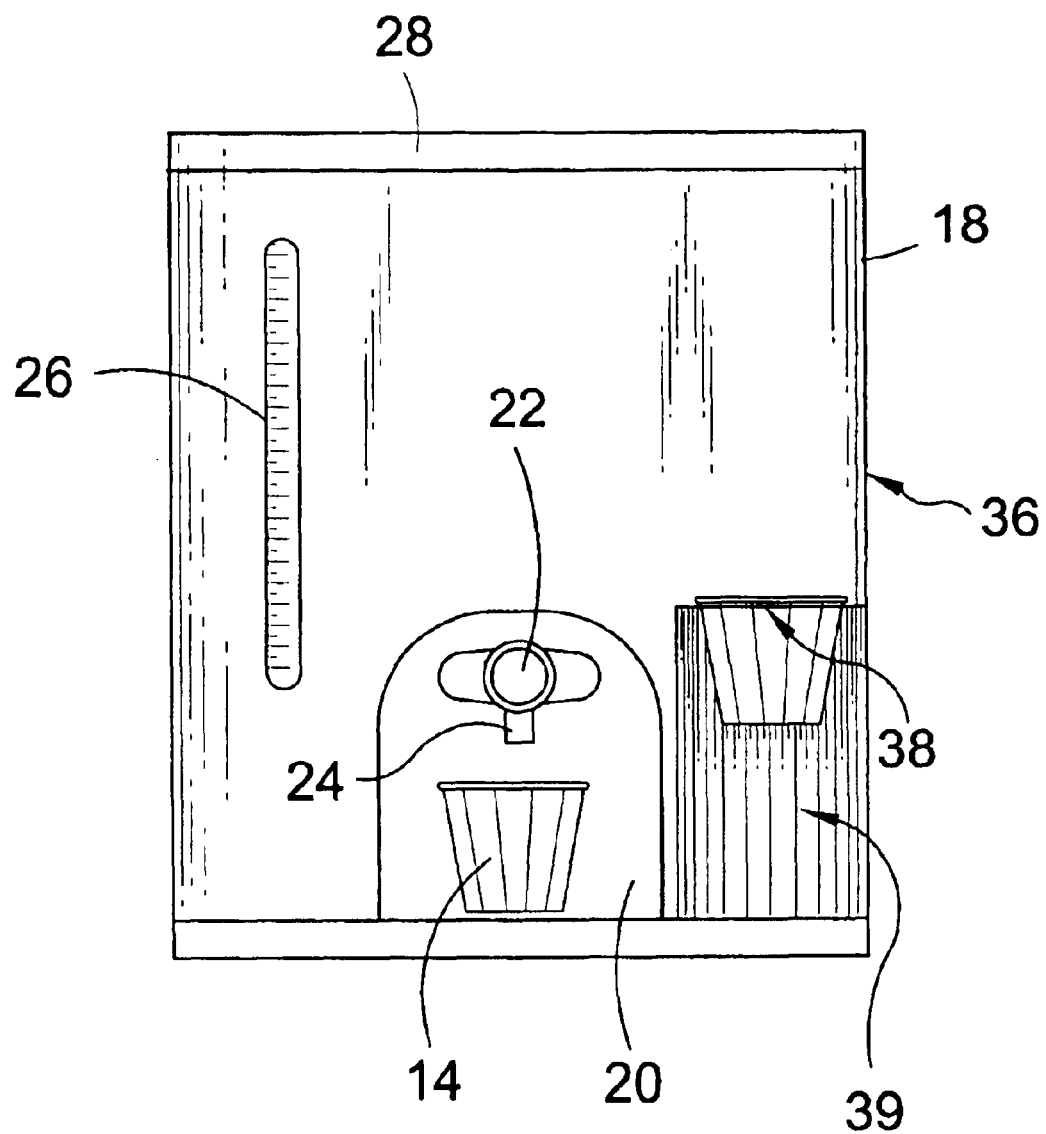
FIG. 5 is a front view of the mouthwash dispenser of the present invention.

FIG. 5 is a front view of an alternate embodiment of the mouthwash dispenser of the present invention. This alternate embodiment includes a housing 18 forming an inner cavity 34 and a lid 28 for selectively sealing the inner cavity. The lid 28 fits over an opening in the housing 18 leading to the inner cavity to seal the mouthwash within the inner cavity. The housing 18 may be transparent, translucent or opaque. The opaque housing 18 has a vertical indicator 26 providing a visual indicator for viewing the quantity of fluid remaining in the reservoir. The display 26 is preferably formed from a transparent material. However, any display device able to clearly and easily display the remaining amount of mouthwash 32 contained within the housing 18 for viewing by a user may be used. The housing also contains a recessed area 20. The recessed area 20 is provided to receive the receptacle into which mouthwash 32 is dispensed. The recessed area 20 further contains the control mechanism 22 therein. A spout 24 also positioned extending into the recessed area 20. The control mechanism 22 is connected to the spout 24 for controlling the flow of mouthwash 32 to the spout 24. The control mechanism 22 in this embodiment is a button. However, any device able to selectively block the flow of mouthwash to the spout 24 may be used. When the button is depressed, mouthwash 32 is allowed to flow freely from the inner cavity 34 to the spout 24 and thereafter into a receptacle 14. When the button is released, the flow of mouthwash to the spout 24 is prevented. The housing 18 in this alternate embodiment further contains a receptacle dispenser 36 positioned adjacent the recess. The receptacle dispenser 36 is contained within the housing 18. Receptacles 14 are dispensed from the receptacle dispenser 36 through a receptacle dispensing recess 38 and into a receiving area 39.

The receptacle dispenser 36 dispenses receptacles 14 through the dispensing recess 38 and into the receiving area 39. The user 12 removes the receptacle 14 from the dispensing recess 38 and places the receptacle 14 into the recessed area 20. Upon removal of a receptacle 14 through the recess 38, another receptacle is caused to be at least partially received in the receiving area 39 until the supply of receptacles is finished. Thereafter, the user 12 depresses the control mechanism 22. The pathway between the inner cavity 34 and the spout 24 is opened and mouthwash 32 is allowed to flow from the inner cavity 34 through a tube 33 to the spout 24. The mouthwash 32 is then dispensed through the spout 24 into the receptacle 14 that was placed into the recessed area 20 by the user 12. When the user 12 determines enough mouthwash 32 is dispensed, the user 12 removes his hand from the control mechanism 22 thereby closing the pathway connecting the inner cavity 34 with the spout 24 and preventing the flow of mouthwash therethrough.

Figure 6:
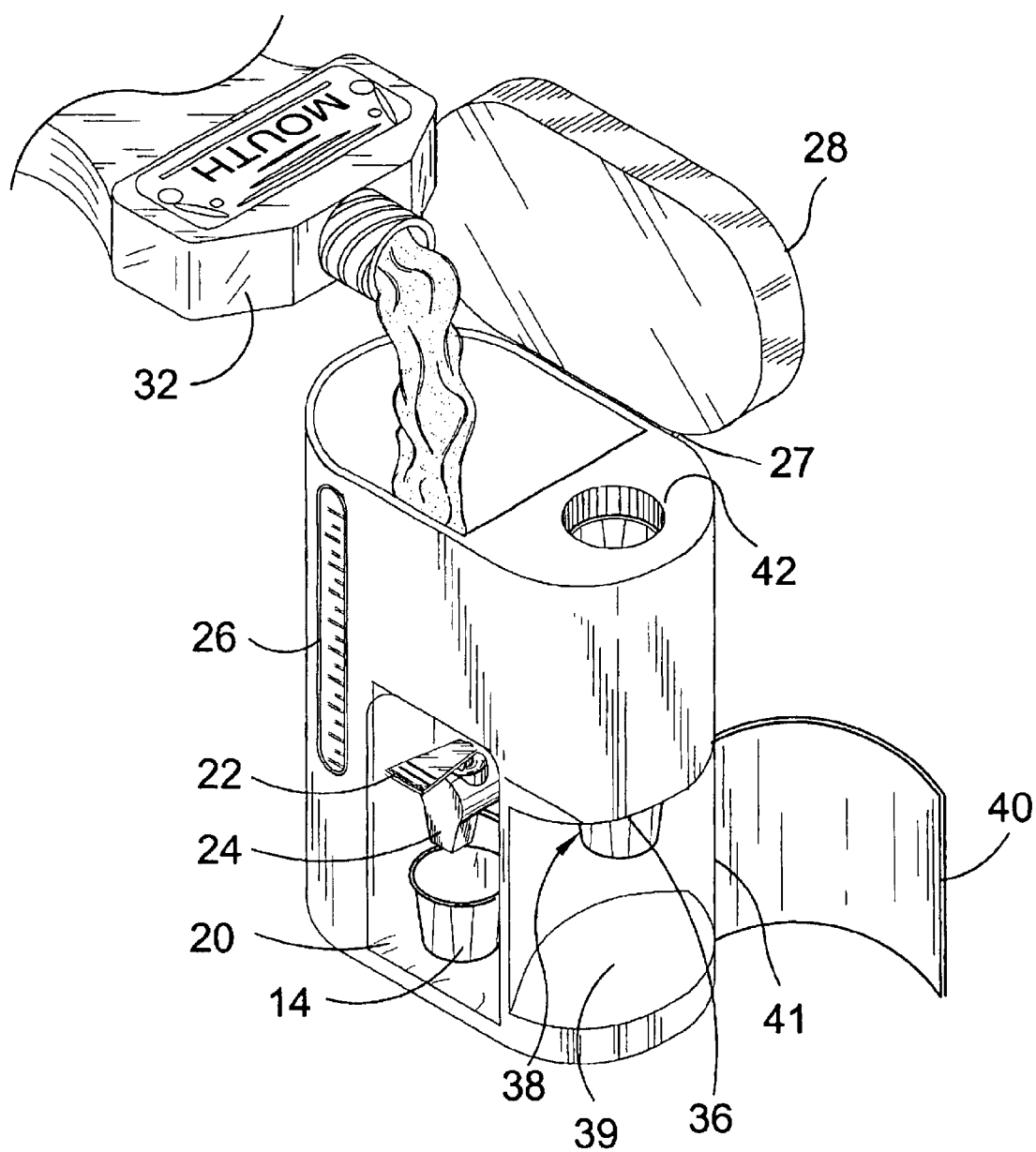
FIG. 6 is a right side perspective view of the mouthwash dispenser of the present invention.

FIG. 6 is a right perspective view of an alternate embodiment of the mouthwash dispenser of the present invention. This alternate embodiment includes a housing 18 forming an inner cavity 34 and a lid 28 for selectively sealing the inner cavity 34. The lid 28 is attached to the top of the housing 18 by a hinge 27. The lid 28 fits over an opening in the housing 18 leading to the inner cavity to seal the mouthwash within the inner cavity. The housing 18 may be transparent, translucent or opaque. The opaque housing 18 has a vertical indicator 26 providing a visual indicator for viewing the quantity of fluid remaining in the reservoir. The display 26 is preferably formed from a transparent material. However, any display device able to clearly and easily display the remaining amount of mouthwash 32 contained within the housing 18 for viewing by a user may be used. The housing also contains a recessed area 20. The recessed area 20 is provided to receive the receptacle into which mouthwash 32 is dispensed. The recessed area 20 further contains the control mechanism 22 therein. A spout 24 also positioned extending into the recessed area 20. The control mechanism 22 is connected to the spout 24 for controlling the flow of mouthwash 32 to the spout 24. The control mechanism 22 in this embodiment is a button. However, any device able to selectively block the flow of mouthwash to the spout 24 may be used. When the button is depressed, mouthwash 32 is allowed to flow freely from the inner cavity 34 to the spout 24 and thereafter into a receptacle 14. When the button is released, the flow of mouthwash to the spout 24 is prevented. The housing 18 in this alternate embodiment further contains a receptacle dispenser 36 positioned adjacent the recess. The receptacle dispenser 36 is housed within the housing 18. When the lid 28 is open the receptacle refill receiving recess 42 is exposed. The user can refill the receptacle dispenser 36 with receptacles 14 when the lid 28 is open by inserting a plurality of receptacles into the recess 42. The receptacles 14 are received and dispensed from the receptacle dispenser 36 through a receptacle dispensing recess 38 into a receiving area 39. The receiving area 39 is also built into the housing 18. The receiving area 39 is selectively accessible through a receptacle door 40. The receptacle door 40 is pivotally attached to the housing 18 by a connection device. When the receptacle door 40 is in an open position, the receptacle recess 38 is exposed thereby allowing a user to remove a receptacle obtained from the receptacle dispenser 36. When the receptacle door 40 is in a closed position, the recess 38 is hidden and the housing 18 of the mouthwash dispenser 10 appears solid.

Figure 7:
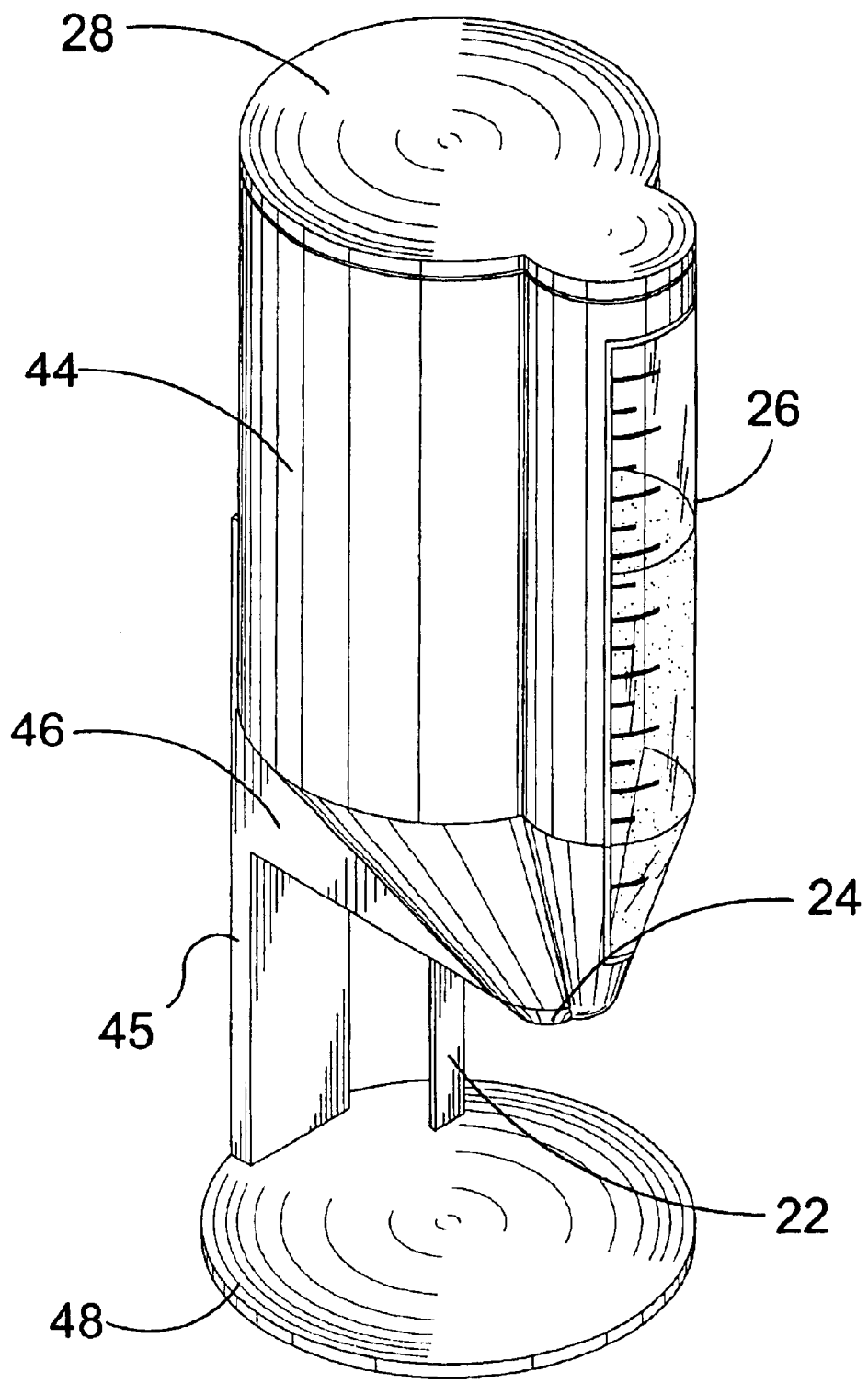
FIG. 7 is a perspective view of an alternate embodiment of the mouthwash dispenser of the present invention.

FIG. 7 is a perspective view of an alternate embodiment of the mouthwash dispenser of the present invention. The mouthwash dispenser 10 has a cylindrical shape compartment housing 44. The compartment housing 44 has an inner cavity 34 with an opening for receiving mouthwash 32 therethrough. The compartment housing 44 is cylindrical on a first end and a lid 28 is fit to selectively cover the opening in the inner cavity 34. The compartment housing 44 further includes a display 26 extending along a side thereof for displaying the amount of mouthwash 32 remaining within the inner cavity 34 of the compartment housing 44. On a side of the compartment housing 44 opposite the lid 28, is connected a control housing 46. The control housing 46 contains a device for dispensing the mouthwash 32 contained within the inner cavity 34 of the compartment housing 44. The control housing includes a control mechanism 22 and a spout 24. The control mechanism shown in this figure is a lever. However, any mechanism able to selectively dispense mouthwash through the spout 24 may be used. When the lever 22 is activated, a retention gate housing within the control housing 46 is moved from a closed position to an open position thereby allowing mouthwash 32 contained within the compartment 44 to be dispensed into a receptacle 14 positioned under the spout 24. When the control mechanism 22 is de-activated, the retention gate moves back into the closed position and prevents further flow of mouthwash from the compartment housing 44. The compartment housing 44 and control housing 46 are attached to a base 48 by an arm 45. The base 48 allows the mouthwash dispenser 10 to be free standing.

Figure 8:
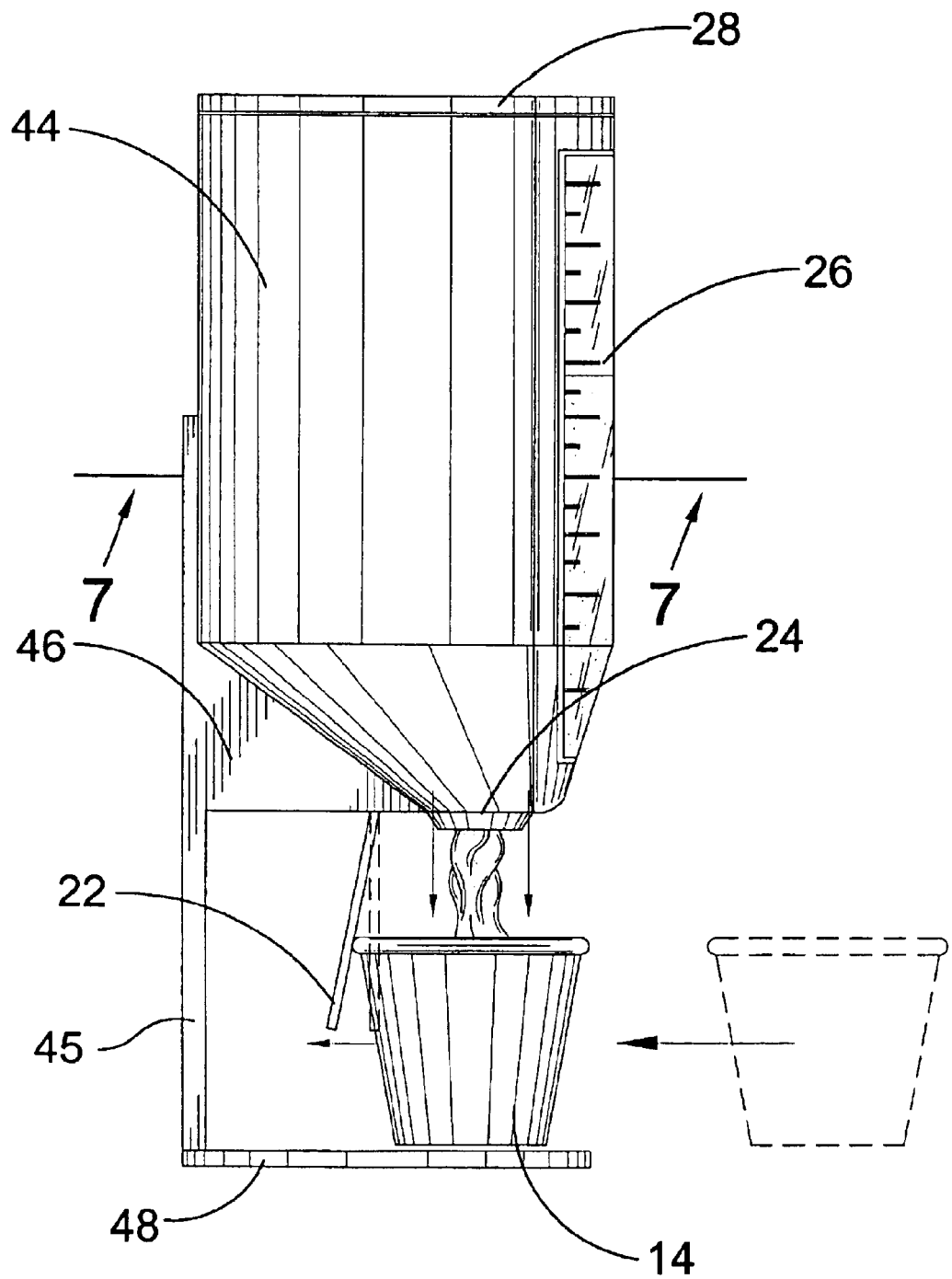
FIG. 8 is a side view of the alternate embodiment of the mouthwash dispenser of the present invention shown in FIG. 7.

FIG. 8 is a side view of the alternate embodiment of the mouthwash dispenser of the present invention. The mouthwash dispenser 10 has a cylindrical shape compartment housing 44. The compartment housing 44 has an inner cavity 34 with an opening for receiving mouthwash 32 therethrough. The compartment housing 44 is cylindrical on a first end and a lid 28 is fit to selectively cover the opening in the inner cavity 34. The compartment housing 44 further includes a display 26 extending along a side thereof for displaying the amount of mouthwash 32 remaining within the inner cavity 34 of the compartment housing 44. On a side of the compartment housing 44 opposite the lid 28, is connected a control housing 46. The control housing 46 contains a device for dispensing the mouthwash 32 contained within the inner cavity 34 of the compartment housing 44. The control housing includes a control mechanism 22 and a spout 24. The control mechanism shown in this figure is a lever. However, any mechanism able to selectively dispense mouthwash through the spout 24 may be used. When the lever 22 is activated, a retention gate housing within the control housing 46 is moved from a closed position to an open position thereby allowing mouthwash 32 contained within the compartment 44 to be dispensed into a receptacle 14 positioned under the spout 24. When the control mechanism 22 is de-activated, the retention gate moves back into the closed position and prevents further flow of mouthwash from the compartment housing 44. The compartment housing 44 and control housing 46 are attached to a base 48 by an arm 45. The base 48 allows the mouthwash dispenser 10 to be free standing.

Figure 9:
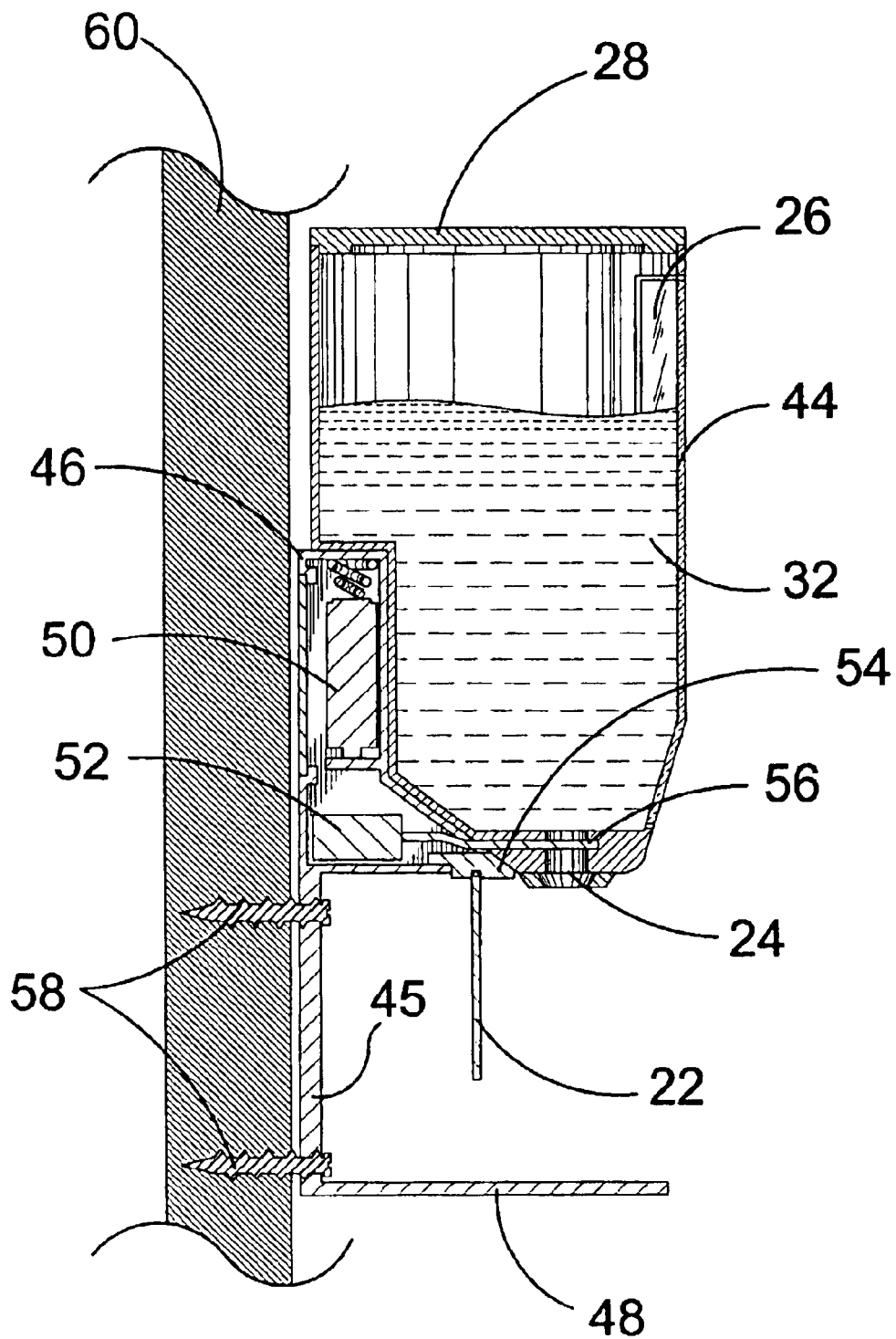
FIG. 9 is a side cross-sectional view of an alternate embodiment of the mouthwash dispenser of the present invention mounted to a wall.

FIG. 9 is a cross-sectional side view of an alternate embodiment of the mouthwash dispenser of the present invention that is wall mounted having a control mechanism operable by a power source. The mouthwash dispenser 10 has a cylindrical shape compartment housing 44. The compartment housing 44 has an inner cavity 34 with an opening for receiving mouthwash 32 therethrough. The compartment housing 44 is cylindrical on a first end and a lid 28 is fit to selectively cover the opening in the inner cavity 34. The compartment housing 44 further includes a display 26 extending along a side thereof for displaying the amount of mouthwash 32 remaining within the inner cavity 34 of the compartment housing 44. On a side of the compartment housing 44 opposite the lid 28, is connected a control housing 46. The control housing 46 contains a device for dispensing the mouthwash 32 contained within the inner cavity 34 of the compartment housing 44. The control housing includes a control mechanism 22 and a spout 24. The control mechanism shown in this figure is a lever 22. However, any mechanism able to selectively dispense mouthwash through the spout 24 may be used. The lever is connected to an actuator 52. The actuator 52 is powered by power source 56. The lever, when depressed signals the actuator 52 by completing the circuit by moving a switch 54 from an open position to a closed position. When the switch 54 is in a closed position, power from the power source 56 is provided to the actuator 52. The actuator 52 moves a retention gate 56 from a closed to an open position thereby allowing mouthwash 32 contained within the compartment 44 to be dispensed into a receptacle 14 placed under the spout 24. When the control mechanism 22 is de-activated the switch 54 returns to an open position, thereby removing power from the actuator 52. The retention gate 56 returns back into the closed position and prevents further flow of mouthwash from the compartment housing 44. The compartment housing 44 and control housing 46 are attached to a base 48 by an arm 45. The user 12 can rest their receptacle 14 on the base 48 while mouthwash 32 is dispensed from the dispenser 10. This embodiment of the mouthwash dispenser 10 further shows itself mounted to the wall 60 by fasteners 58. The fasteners 58 extend through the arm 45 and secured into the wall 60. Any means to fasten the dispense 10 to the wall 60 may be used.

Figure 10:
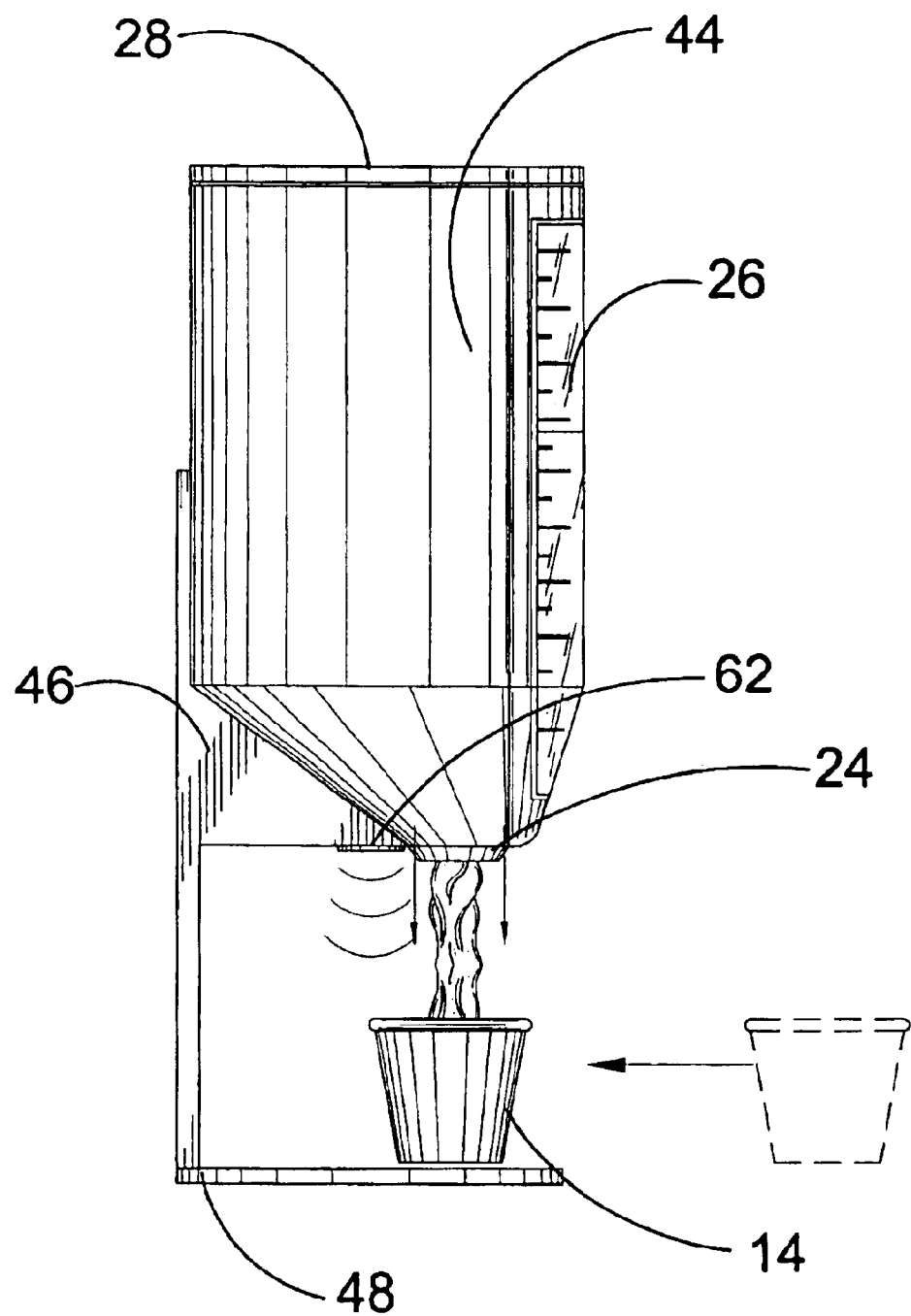
FIG. 10 is a side view of another alternate embodiment of the mouthwash dispenser of the present invention.

FIG. 10 is a side view of another alternate embodiment of the mouthwash dispenser of the present invention. The mouthwash dispenser 10 has a cylindrical shape compartment housing 44. The compartment housing 44 has an inner cavity 34 with an opening for receiving mouthwash 32 therethrough. The compartment housing 44 is cylindrical on a first end and a lid 28 is fit to selectively cover the opening in the inner cavity 34. The compartment housing 44 further includes a display 26 extending along a side thereof for displaying the amount of mouthwash 32 remaining within the inner cavity 34 of the compartment housing 44. On a side of the compartment housing 44 opposite the lid 28, is connected a control housing 46. The control housing 46 contains a device for dispensing the mouthwash 32 contained within the inner cavity 34 of the compartment housing 44. The control housing includes a control mechanism 22 and a spout 24. The control mechanism in this alternate embodiment is an electric eye 62. However, any mechanism able to selectively dispense mouthwash through the spout 24 may be used. The electric eye 62 is connected to an actuator 52. The actuator 52 is powered by power source 56. When the electric eye 62 detects a receptacle 14 thereunder, it signals the actuator 52. Power is then provided from power source 56 to the actuator 52. The actuator 52 moves a retention gate 56 from a closed to an open position thereby allowing mouthwash 32 contained within the compartment 44 to be dispensed into a receptacle 14 placed under the spout 24. When the receptacle 14 is removed from the electric eye 62, power is remove from the actuator 52. The retention gate 56 then returns back into the closed position and prevents further flow of mouthwash from the compartment housing 44. The compartment housing 44 and control housing 46 are attached to a base 48 by an arm 45. The base 48 allows the mouthwash dispenser 10 to be free standing.

Figure 11:
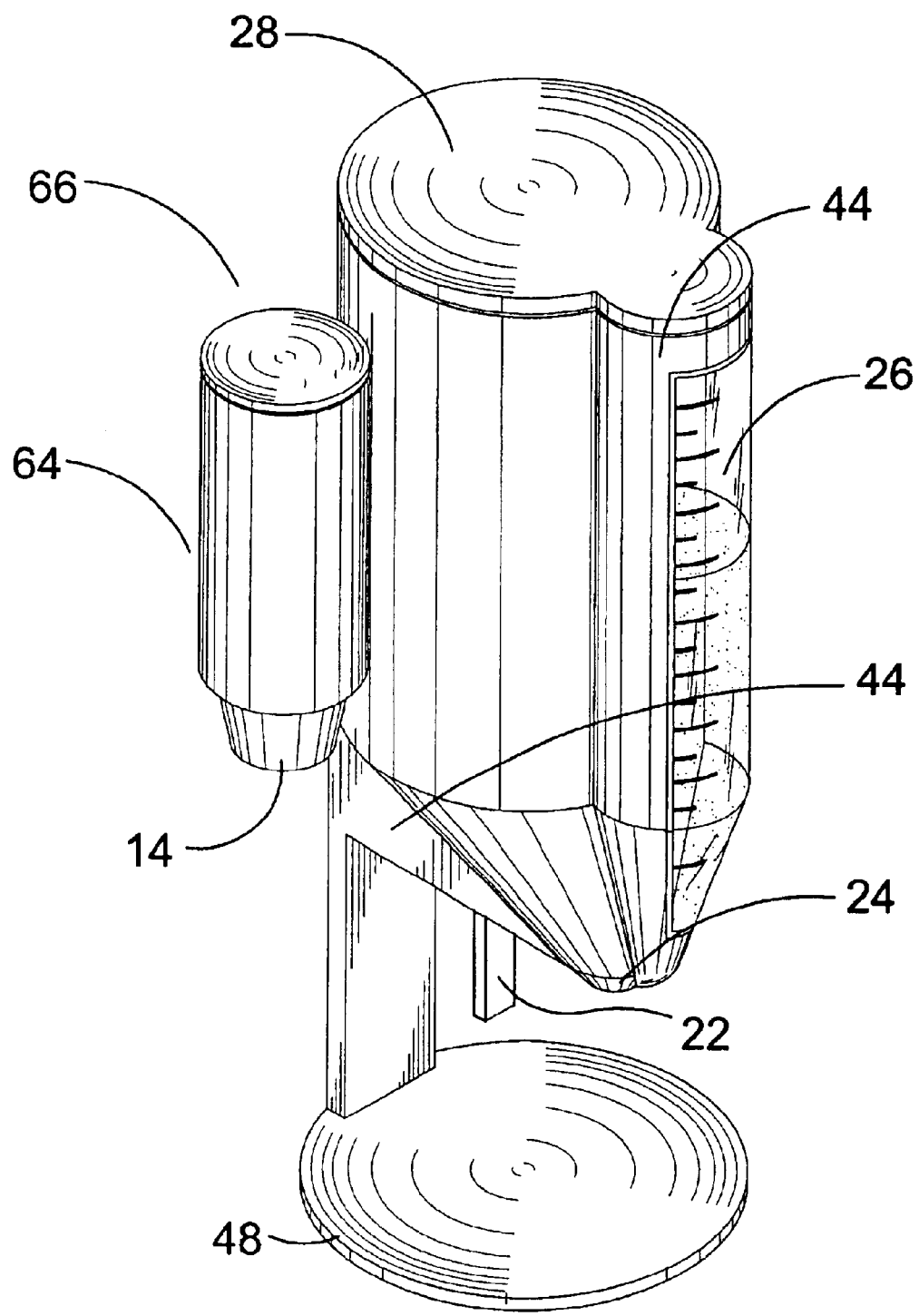
FIG. 11 is a perspective view of the mouthwash dispenser of the present invention shown in FIG. 10 having a receptacle holder attached thereto.

FIG. 11 is a perspective view of the mouthwash dispenser of the present invention having a receptacle holder attached thereto. The mouthwash dispenser 10 has a cylindrical shape compartment housing 44. The compartment housing 44 has an inner cavity 34 with an opening for receiving mouthwash 32 therethrough. The compartment housing 44 is cylindrical on a first end and a lid 28 is fit to selectively cover the opening in the inner cavity 34. The compartment housing 44 further includes a display 26 extending along a side thereof for displaying the amount of mouthwash 32 remaining within the inner cavity 34 of the compartment housing 44. The compartment housing 44 has an external receptacle dispenser 64 attached thereto for dispensing receptacles 14. The external receptacle dispenser 64 has a lid 6 for covering the receptacles 14 and also for allowing easy access for refilling the receptacles 14 when required. On a side of the compartment housing 44 opposite the lid 28, is connected a control housing 46. The control housing 46 contains a device for dispensing the mouthwash 32 contained within the inner cavity 34 of the compartment housing 44. The control housing includes a control mechanism 22 and a spout 24. The control mechanism shown in this figure is a lever. However, any mechanism able to selectively dispense mouthwash through the spout 24 may be used. When the lever 22 is activated, a retention gate housing within the control housing 46 is moved from a closed position to an open position thereby allowing mouthwash 32 contained within the compartment 44 to be dispensed into a receptacle 14 positioned under the spout 24. When the control mechanism 22 is de-activated, the retention gate moves back into the closed position and prevents further flow of mouthwash from the compartment housing 44. The compartment housing 44 and control housing 46 are attached to a base 48 by an arm 45. The base 48 allows the mouthwash dispenser 10 to be free standing.

Figure 12:
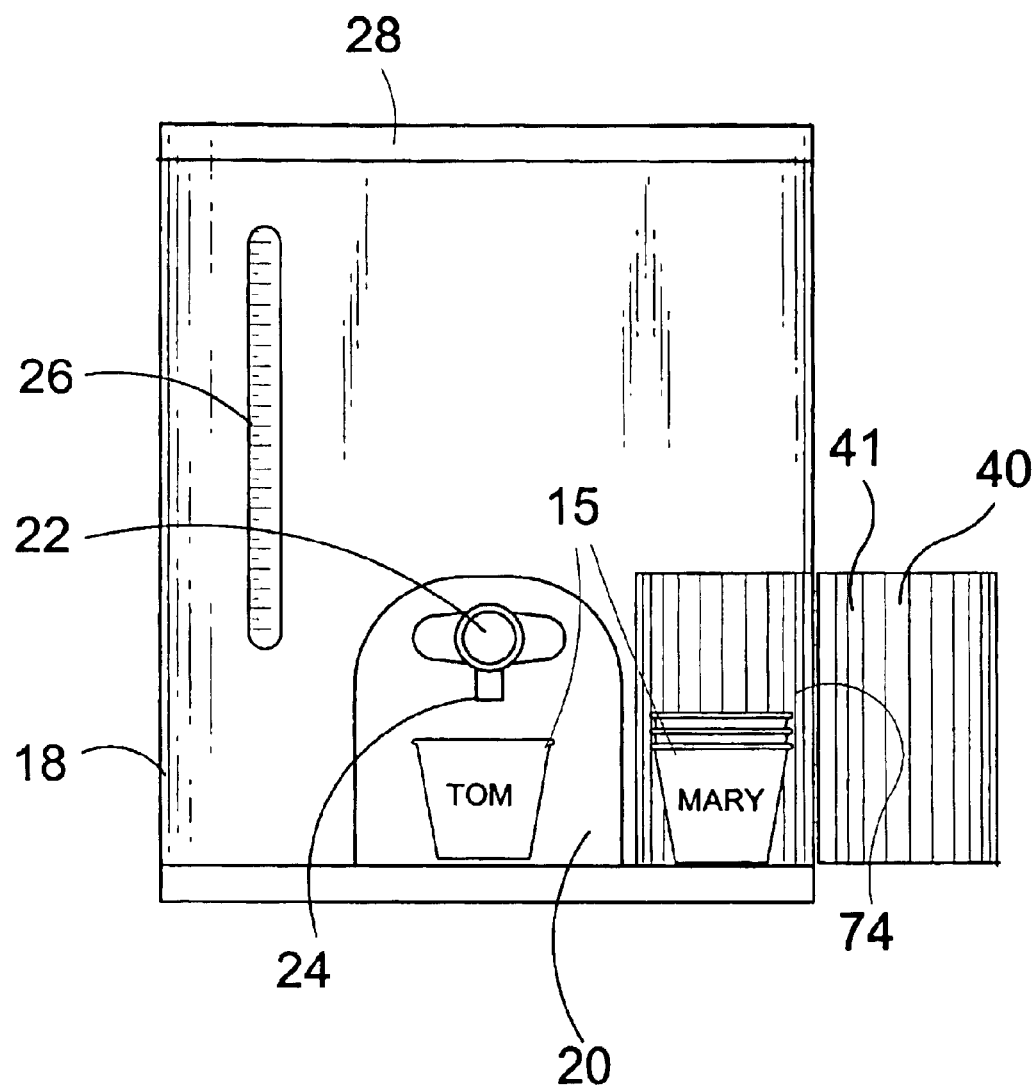
FIG. 12 is a front view the mouthwash dispenser of the present invention shown in FIGS. 1–6 having re-useable receptacles are associated therewith.

FIG. 12 is a front view of an alternate embodiment of the mouthwash dispenser of the present invention whereby re-useable receptacles are associated therewith. This alternate embodiment includes a housing 18. The housing has an inner cavity 34 having an opening for allowing the inner cavity to receive mouthwash therethrough. A lid is provided to selectively seal the opening in the inner cavity 34. The housing 18 may be transparent, translucent or opaque. The opaque housing 18 has a vertical indicator 26 providing a visual indicator for viewing the quantity of fluid remaining in the reservoir. The display 26 is preferably formed from a transparent material. However, any display device able to clearly and easily display the remaining amount of mouthwash 32 contained within the housing 18 for viewing by a user may be used. The housing also contains a recessed area 20. The recessed area 20 is provided to receive the receptacle into which mouthwash 32 is dispensed. The recessed area 20 further contains the control mechanism 22 therein. A spout 24 also positioned extending into the recessed area 20. The control mechanism 22 is connected to the spout 24 for controlling the flow of mouthwash 32 to the spout 24. The control mechanism 22 in this embodiment is a button. However, any device able to selectively block the flow of mouthwash to the spout 24 may be used. When the button is depressed, mouthwash 32 is allowed to flow freely from the inner cavity 34 to the spout 24 and thereafter into a receptacle 14. When the button is released, the flow of mouthwash to the spout 24 is prevented. The housing 18 has a receptacle compartment 74. The receptacle compartment 74 is also built into the housing 18 and is enclosed by receptacle door 40. The receptacle door 40 is pivotally connected to the housing 18 by a connection device 39. When the receptacle door 40 is in an open position, the receptacle storage compartment 74 is exposed thereby allowing a user to remove a receptacle therefrom. When the receptacle door 40 is in a closed position, the storage compartment 74 is hidden and the housing 18 of the mouthwash dispenser 10 appears solid. The receptacle storage compartment 74 is suitable for storing reusable receptacles 15. Each reusable receptacle 15 comes with an identification means for giving notification to a user 12 of the ownership of each reusable receptacle 15. The reusable receptacles are rinsed after use and replaced within the receptacle storage compartment 74.

Figure 13:
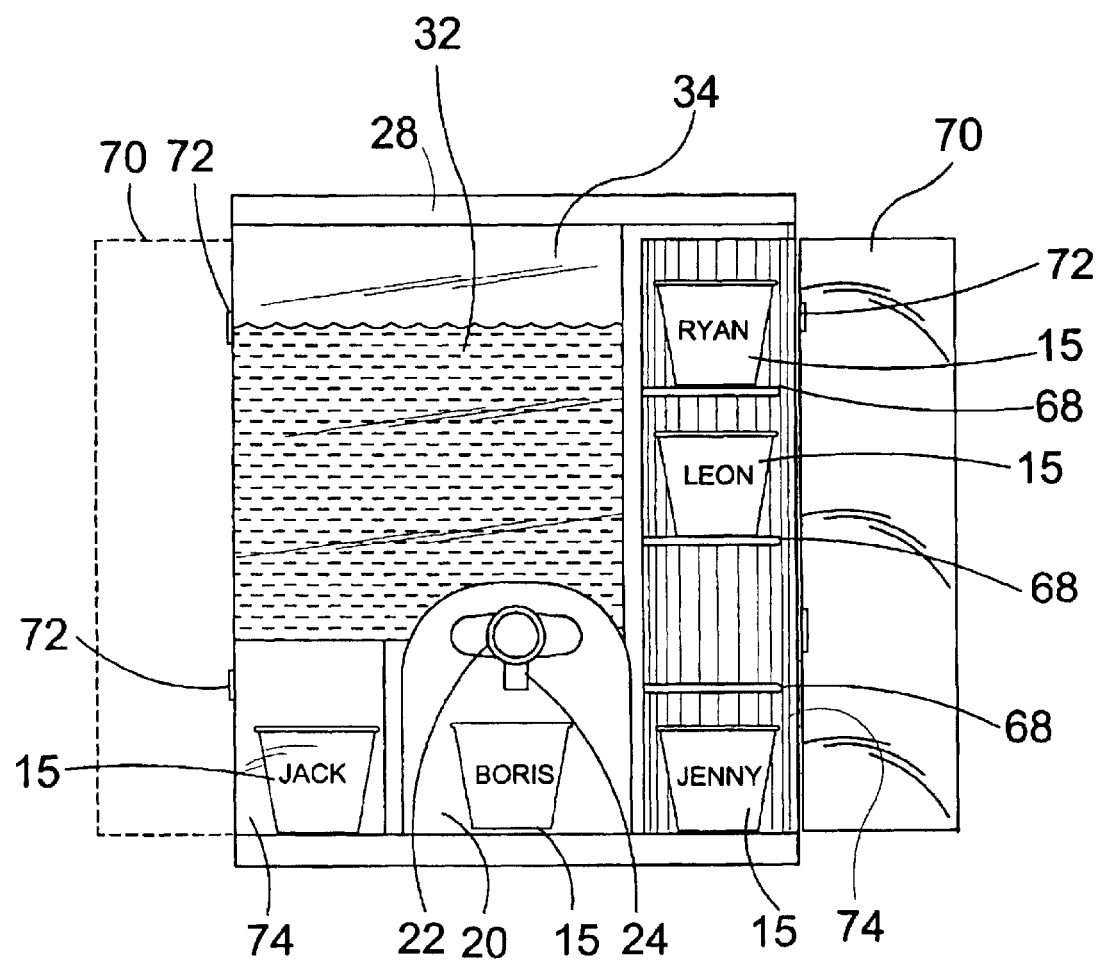
FIG. 13 is a front view of another alternate embodiment of the mouthwash dispense of the present invention having a respective storage areas for each of a plurality of re-useable receptacles.

FIG. 13 is a front view of yet another alternate embodiment of the mouthwash dispense of the present invention having storage areas for re-useable receptacles. The housing 18 has a receptacle compartment 74 extending along one or both sides of the housing 18. The receptacle compartments 74 contain at least one shelf 68 therein. The shelf 68 is contained within the receptacle compartment 74 an provides for storage of a re-useable receptacle 15. The receptacle compartments 74 are selectively enclosed by a door 70. The door 70 is pivotally attached to the housing 18 by a connection device 72. A user 12 can open the door 70 and remove his/her own reusable receptacle 15 identified by color or name or other means. The receptacle is positioned in the recessed area 20 for receiving mouthwash 32 contained within the housing 18. Thereafter the user rinses and cleans the reusable receptacle 15 and replaces it on a shelf 68 in the receptacle storage compartment 74 for subsequent use at a later time.

Figure 14:
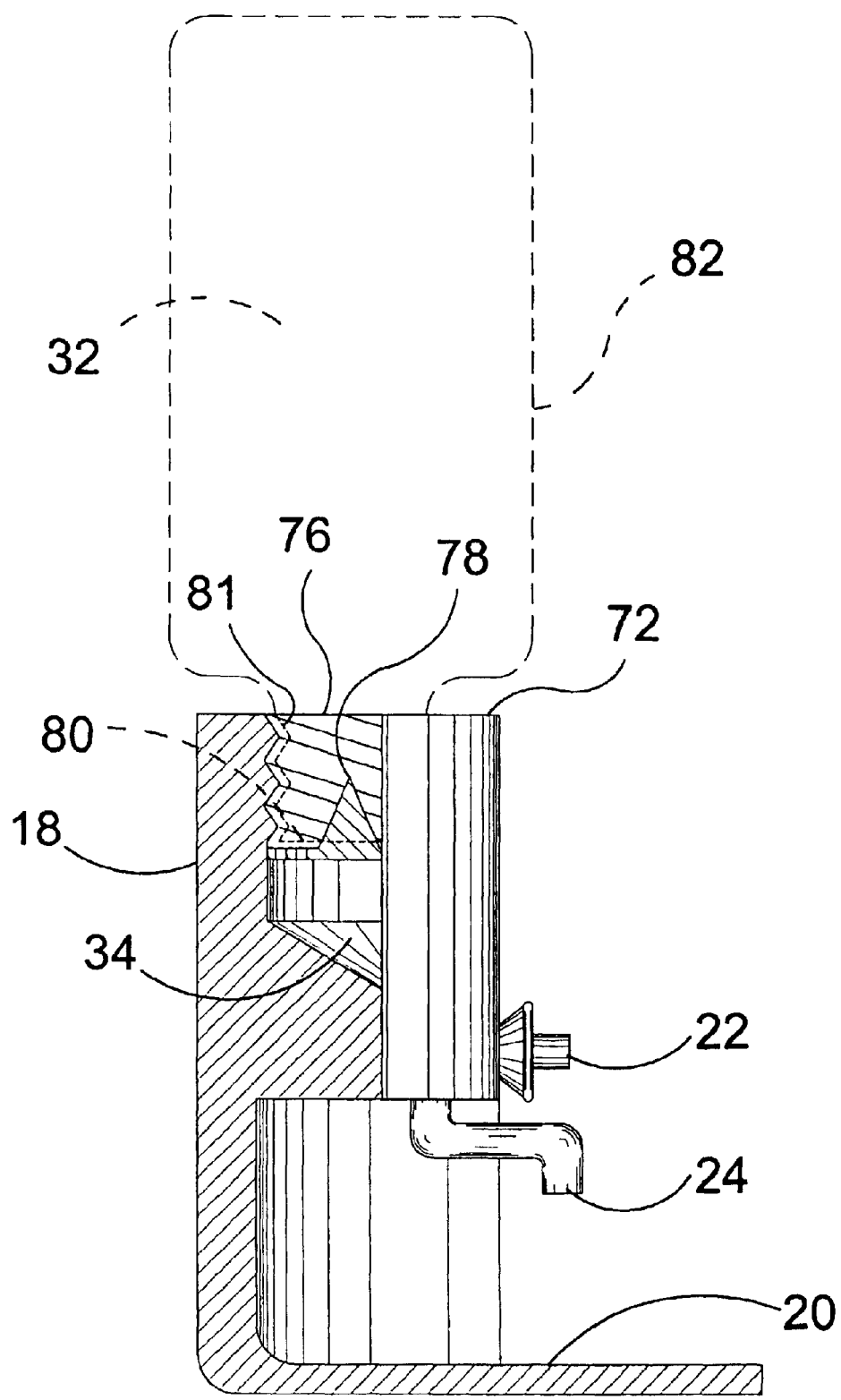
FIG. 14 is a perspective view of the mouthwash dispenser of the present invention shown in FIGS. 1–6 having an alternate form of opening for receiving mouthwash.

FIG. 14 is a perspective view of the mouthwash dispenser of the present invention using a mouthwash bottle 82 for the containment of the mouthwash 32. The mouthwash dispenser 10 of the present invention has a housing 18. The housing 18 has an entirely enclosed inner cavity 34 for receiving mouthwash 32. The inner cavity 34 is accessed by fill spout 76. Fill spout 76 is preferably located in an easily accessible location. In this embodiment the fill spout 76 is on a top side of the housing 18. Fill spout 76 includes a puncturing device 78. The puncturing device 78 is provided to puncture the seal 80 of a mouthwash bottle 82 when received by the fill spout 76. The fill spout 76 and a spout 81 of a bottle of mouthwash have substantially the same diameter. When the mouthwash needs to be refilled, the bottle spout 81 is received by the fill spout 76. The puncture device 78 punctures the seal 80 covering the spout 81 of the bottle 82 and mouthwash is thereby allowed to flow from the bottle 82 through the fill spout 76 and into the inner cavity 34. The housing 18 has a recessed area 20. Within the recessed area 20 is a control mechanism 22 for controlling the disbursement of mouthwash 32 and a spout 24 for dispensing mouthwash therethrough. The dispensing of the mouthwash through the spout is controlled by the control mechanism 22. The recessed area 20 is of a size able to receive a receptacle 14 into which the mouthwash 32 is to be dispensed.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A mouthwash dispenser consisting of:
   a) a housing having an inner cavity able to retain mouthwashing liquid therein and a top opening for pouring said liquid into said inner cavity;
   b) a lid for selectively sealing said top opening and thereby enclosing the liquid in said inner cavity of said housing;
   c) control means extending from said housing for controlling the dispensing of said liquid from said inner cavity;
   d) a spout connected to said inner cavity for dispensing liquid from said inner cavity, wherein said control means is moveable between a first position preventing a flow of liquid from said inner cavity to said spout and a second position for allowing a flow of liquid from said inner cavity to said spout; and
   e) said housing having a compartment on one side thereof, said compartment containing shelves for storing reusable cups, and a door pivotable between a position enclosing said compartment and a position exposing said compartment, said cups on said shelves being identifiable for the user of each cup.

2. The mouthwash dispenser as recited in claim 1, further comprising a tube for connecting said inner cavity with said spout.

3. The mouthwash dispenser as recited in claim 2, wherein said control means includes a sealing element, said sealing element for obstructing the flow of the liquid through said tube when said control means is in said first closed position, and said sealing element allowing flow of the liquid through said tube when said control means is in a said second open position.

4. The mouthwash dispenser as recited in claim 2, wherein said housing is transparent.

5. The mouthwash dispenser as recited in claim 2, wherein said housing is translucent.

6. The mouthwash dispenser as recited in claim 2, wherein said housing is opaque.

7. The mouthwash dispense as recited in claim 2 wherein said control means further comprises:
   a) a lever;
   b) a switch;
   c) an actuator;
   d) a power source; and
   e) a retention gate, wherein said lever is connected to said switch, and when said lever is activated, said switch connects said power source to said actuator, whereby said power source activates said actuator to move said retention gate from a first closed position to a second open position.

8. The mouthwash dispense as recited in claim 2 wherein said control means further comprises:
   a) an electric eye;
   b) a switch;
   c) an actuator;
   d) a power source; and
   e) a retention gate, wherein said electric eye is connected to said switch, and upon detecting a receptacle beneath said electric eye, said electric eye controls said switch to connect said power source to said actuator, whereby said actuator causes said retention gate to move from a first closed position to a second open position.

9. The mouthwash dispenser as recited in claim 1 wherein said control means further comprises:
 a) a lever;
 b) a switch; and
 c) a retention gate, wherein said lever is connected to said switch, and when said lever is activated, said switch causes said retention gate to move from a first closed position to a second open position thereby allowing the liquid to flow through said spout.

10. The mouthwash dispenser as recited in claim 1 further comprising a display for displaying the contents of liquid contained within said inner cavity.

11. The mouthwash dispenser as recited in claim 1, further comprising a hinge for pivotally connecting said lid to said housing.

12. The mouthwash dispenser as recited in claim 1, further comprising means for securing said dispenser to a vertical surface.

* * * * *